US008622985B2

(12) United States Patent
Ellstrom

(10) Patent No.: US 8,622,985 B2
(45) Date of Patent: Jan. 7, 2014

(54) ARRANGEMENT FOR USE WITH A MEDICAL DEVICE

(75) Inventor: Anna Ellstrom, Molndal (SE)

(73) Assignee: Carmel Pharma AB, Gothenburg (SE)

(*) Notice: Subject to any disclaimer, the term of this patent is extended or adjusted under 35 U.S.C. 154(b) by 0 days.

(21) Appl. No.: 11/762,528

(22) Filed: Jun. 13, 2007

(65) Prior Publication Data

US 2008/0312633 A1 Dec. 18, 2008

(51) Int. Cl.
*A61B 19/00* (2006.01)
*A61J 1/00* (2006.01)
*A61J 1/05* (2006.01)
*A61J 1/14* (2006.01)

(52) U.S. Cl.
USPC ........... 604/405; 604/411; 604/414; 604/415; 604/416

(58) Field of Classification Search
USPC ........... 128/DIG. 24; 141/329, 346, 363, 369, 141/372, 383; 215/234, 247, 248, 249, 250, 215/DIG. 8; 604/403, 405, 411, 414, 415, 604/416, 905
See application file for complete search history.

(56) References Cited

U.S. PATENT DOCUMENTS

| | | | | |
|---|---|---|---|---|
| 1,844,342 | A | | 2/1932 | Berman |
| 2,010,417 | A | | 8/1935 | Schwab |
| 2,697,438 | A | | 12/1954 | Hickey |
| 2,717,599 | A | | 9/1955 | Huber |
| 3,064,651 | A | | 11/1962 | Henderson |
| 3,071,135 | A | | 1/1963 | Baldwin et al. |
| 3,308,822 | A | | 3/1967 | DeLuca |
| 3,316,908 | A | | 5/1967 | Burke |
| 3,340,671 | A | * | 9/1967 | Loo ................................ 53/426 |
| 3,390,677 | A | | 7/1968 | Razimbaud |
| 3,448,740 | A | | 6/1969 | Figge |
| 3,542,240 | A | | 11/1970 | Solowey |
| 3,783,895 | A | | 1/1974 | Weichselbaum |
| 3,788,320 | A | | 1/1974 | Dye |
| 3,822,700 | A | | 7/1974 | Pennington |
| 3,938,520 | A | | 2/1976 | Scislowicz et al. |
| 3,976,073 | A | | 8/1976 | Quick et al. |
| 4,096,860 | A | | 6/1978 | McLaughlin |
| 4,296,786 | A | | 10/1981 | Brignola |
| D270,568 | S | | 9/1983 | Armstrong |

(Continued)

FOREIGN PATENT DOCUMENTS

| | | |
|---|---|---|
| AU | 200112863 | 5/2003 |
| DE | 2005519 | 10/1979 |

(Continued)

OTHER PUBLICATIONS

Taiwan Search Report for Taiwan Patent Application 092106323,dated Mar. 21, 2003 (4 pages).

(Continued)

*Primary Examiner* — Adam Marcetich
(74) *Attorney, Agent, or Firm* — Servilla Whitney LLC

(57) ABSTRACT

The invention relates to an arrangement for use with a medical device which arrangement comprises a shield for a tip of a needle member of a medical device. The arrangement comprises a filter for filtering gas to be transferred out from or into the medical device via the needle member when the arrangement is interconnected with the medical device. The filter is integrated with or constitutes at least a portion of the needle member tip shield.

17 Claims, 5 Drawing Sheets

(56) References Cited

U.S. PATENT DOCUMENTS 4,490,139 A 12/1984 Huizenga et al.
4,507,118 A * 3/1985 Dent .............................. 604/198
4,516,967 A 5/1985 Kopfer
4,524,809 A * 6/1985 Dent .................................. 141/1
4,564,054 A * 1/1986 Gustavsson ................... 141/329
4,573,967 A 3/1986 Hargrove et al.
4,576,211 A 3/1986 Valentini et al.
4,581,016 A 4/1986 Gettig
4,582,223 A 4/1986 Kobe
4,588,403 A * 5/1986 Weiss et al. ................... 604/411
4,600,040 A 7/1986 Naslund
4,623,343 A 11/1986 Thompson
4,629,455 A 12/1986 Kanno
4,632,673 A 12/1986 Tiitola et al.
4,636,204 A 1/1987 Christopherson et al.
4,673,400 A 6/1987 Martin
4,673,404 A * 6/1987 Gustavsson ................... 604/411
4,737,150 A * 4/1988 Baeumle et al. .............. 604/198
4,752,287 A 6/1988 Kurtz et al.
4,768,568 A * 9/1988 Fournier et al. ............... 141/286
4,792,329 A * 12/1988 Schreuder ....................... 604/90
4,804,015 A 2/1989 Albinsson
4,822,340 A * 4/1989 Kamstra ....................... 604/135
4,826,492 A 5/1989 Magasi
4,834,717 A 5/1989 Haber et al.
4,842,585 A 6/1989 Witt
4,850,978 A 7/1989 Dudar et al.
4,864,717 A 9/1989 Baus, Jr.
4,872,494 A 10/1989 Coccia
4,878,897 A 11/1989 Katzin
4,889,529 A 12/1989 Haindl
4,898,209 A 2/1990 Zbed
4,909,290 A 3/1990 Coccia
4,932,937 A 6/1990 Gustavsson et al.
4,944,736 A 7/1990 Holtz
4,964,855 A 10/1990 Todd et al.
4,982,769 A * 1/1991 Fournier et al. ................. 141/98
4,994,048 A 2/1991 Metzger
4,997,083 A 3/1991 Loretti et al.
5,017,186 A 5/1991 Arnold
5,041,105 A 8/1991 D'Alo et al.
5,061,264 A 10/1991 Scarrow
5,071,413 A 12/1991 Utterberg
5,122,116 A 6/1992 Kriesel et al.
5,122,123 A 6/1992 Vaillancourt
5,137,524 A 8/1992 Lynn et al.
5,147,309 A * 9/1992 Hemmerich et al. ......... 604/122
5,158,554 A 10/1992 Jepson et al.
5,176,673 A 1/1993 Marrucchi
5,199,947 A 4/1993 Lopez et al.
5,201,725 A 4/1993 Kling
5,207,658 A 5/1993 Rosen et al.
5,232,109 A 8/1993 Tirrell et al.
5,254,097 A 10/1993 Schock et al.
5,279,576 A 1/1994 Loo et al.
5,279,583 A 1/1994 Shober, Jr. et al.
5,279,605 A 1/1994 Karrasch et al.
5,308,347 A 5/1994 Sunago et al.
5,312,366 A 5/1994 Vailancourt
5,328,480 A 7/1994 Melker et al.
5,334,163 A 8/1994 Sinnett
5,356,406 A 10/1994 Schraga
5,385,545 A 1/1995 Kriesel et al.
5,385,547 A 1/1995 Wong et al.
5,389,085 A 2/1995 D'Alessio et al.
5,405,326 A 4/1995 Haber et al.
5,445,630 A 8/1995 Richmond
5,447,501 A 9/1995 Karlsson et al.
5,456,675 A 10/1995 Wolbring et al.
5,470,522 A 11/1995 Thome et al.
5,478,328 A 12/1995 Silverman et al.
5,478,337 A 12/1995 Okamoto et al.
5,492,531 A 2/1996 Post et al.
5,514,117 A 5/1996 Lynn
5,515,871 A 5/1996 Bittner et al.
5,536,259 A 7/1996 Utterberg
5,575,780 A 11/1996 Saito
5,593,028 A 1/1997 Haber et al.
5,613,954 A 3/1997 Nelson et al.
5,632,735 A 5/1997 Wyatt et al.
5,647,845 A 7/1997 Haber et al.
5,685,866 A 11/1997 Lopez
5,752,942 A 5/1998 Doyle et al.
5,766,147 A 6/1998 Sancoff et al.
5,766,211 A 6/1998 Wood et al.
5,782,383 A * 7/1998 Robinson ........................ 222/81
5,782,872 A 7/1998 Muller
5,795,336 A 8/1998 Romano et al.
5,817,083 A 10/1998 Shemesh et al.
5,820,609 A 10/1998 Saito
5,827,262 A 10/1998 Neftel et al.
5,837,262 A 11/1998 Golubev et al.
5,875,931 A * 3/1999 Py ................................. 222/137
5,879,345 A 3/1999 Aneas
5,897,526 A 4/1999 Vaillancourt
5,934,510 A 8/1999 Anderson
5,984,899 A 11/1999 D'Alessio et al.
6,063,068 A 5/2000 Fowles et al.
D427,308 S 6/2000 Zinger
6,070,623 A 6/2000 Aneas
6,071,270 A 6/2000 Fowles et al.
6,090,091 A 7/2000 Fowles et al.
6,113,068 A 9/2000 Ryan
6,113,583 A 9/2000 Fowles et al.
6,142,446 A 11/2000 Leinsing
6,146,362 A 11/2000 Turnbull et al.
6,171,293 B1 * 1/2001 Rowley et al. ................ 604/403
6,209,738 B1 4/2001 Jansen et al.
6,221,065 B1 4/2001 Davis
6,245,056 B1 6/2001 Walker et al.
D445,501 S 7/2001 Niedospial, Jr.
6,253,804 B1 7/2001 Safabash
6,258,078 B1 7/2001 Thilly
6,280,430 B1 * 8/2001 Neftel et al. .................. 604/411
6,387,074 B1 5/2002 Horppu et al.
6,453,956 B2 9/2002 Safabash
6,471,674 B1 10/2002 Emig et al.
6,517,523 B1 2/2003 Kaneko et al.
6,537,263 B1 3/2003 Aneas
6,571,837 B2 6/2003 Jansen et al.
6,591,876 B2 7/2003 Safabash
6,644,367 B1 11/2003 Savage et al.
6,685,692 B2 2/2004 Fathallah
6,715,520 B2 4/2004 Andreasson et al.
6,761,286 B2 * 7/2004 Py et al. ........................ 222/105
D495,416 S 8/2004 Dimeo et al.
6,786,244 B1 9/2004 Jones
D506,256 S 6/2005 Miyoshi et al.
6,960,194 B2 11/2005 Hommann et al.
7,000,806 B2 * 2/2006 Py et al. ..................... 222/386.5
7,080,672 B2 7/2006 Fournier et al.
7,297,140 B2 11/2007 Orlu et al.
D570,477 S 6/2008 Gallogly et al.
D572,820 S 7/2008 Gallogly et al.
D577,438 S 9/2008 Gallogly et al.
D577,822 S 9/2008 Gallogly et al.
D582,033 S 12/2008 Baxter et al.
D605,755 S 12/2009 Baxter et al.
7,703,486 B2 4/2010 Costanzo
D616,984 S 6/2010 Gilboa
7,744,581 B2 6/2010 Wallen et al.
2001/0021825 A1 9/2001 Becker et al.
2001/0025671 A1 10/2001 Safabash
2002/0002352 A1 1/2002 Becker et al.
2002/0082586 A1 6/2002 Finley et al.
2002/0127150 A1 9/2002 Sasso
2002/0177819 A1 11/2002 Barker et al.
2003/0010717 A1 1/2003 Brugger et al.
2003/0070726 A1 4/2003 Andreasson et al.
2003/0106610 A1 6/2003 Roos et al.
2003/0107628 A1 6/2003 Fowles et al.
2003/0199846 A1 10/2003 Fowles et al.
2003/0233083 A1 12/2003 Houwaert et al.
2004/0116858 A1 6/2004 Heinz et al.

(56) References Cited

U.S. PATENT DOCUMENTS

| | | | | |
|---|---|---|---|---|
| 2004/0199139 | A1 | 10/2004 | Fowles et al. | |
| 2004/0215147 | A1* | 10/2004 | Wessman et al. | 604/187 |
| 2004/0267228 | A1* | 12/2004 | Hattori et al. | 604/406 |
| 2005/0215977 | A1 | 9/2005 | Uschold | |
| 2006/0025747 | A1 | 2/2006 | Sullivan et al. | |
| 2006/0106360 | A1 | 5/2006 | Wong | |
| 2006/0111667 | A1* | 5/2006 | Matsuura et al. | 604/93.01 |
| 2006/0157984 | A1 | 7/2006 | Rome et al. | |
| 2006/0186045 | A1 | 8/2006 | Jensen et al. | |
| 2007/0021725 | A1 | 1/2007 | Villette | |
| 2007/0060841 | A1* | 3/2007 | Henshaw | 600/578 |
| 2007/0088313 | A1 | 4/2007 | Zinger et al. | |
| 2007/0106244 | A1 | 5/2007 | Mosler et al. | |
| 2007/0179441 | A1 | 8/2007 | Chevallier | |
| 2007/0270759 | A1 | 11/2007 | Pessin | |
| 2007/0270778 | A9 | 11/2007 | Zinger et al. | |
| 2008/0045919 | A1 | 2/2008 | Jakob et al. | |
| 2008/0103453 | A1 | 5/2008 | Liversidge | |
| 2008/0103485 | A1 | 5/2008 | Kruger | |
| 2008/0172039 | A1 | 7/2008 | Raines | |
| 2008/0223484 | A1 | 9/2008 | Horppu | |
| 2008/0287920 | A1 | 11/2008 | Fangrow et al. | |
| 2008/0312634 | A1 | 12/2008 | Helmerson et al. | |
| 2009/0254042 | A1 | 10/2009 | Gratwohl et al. | |
| 2010/0137827 | A1 | 6/2010 | Warren et al. | |
| 2010/0204671 | A1 | 8/2010 | Kraushaar et al. | |
| 2010/0243099 | A1 | 9/2010 | Yodfat | |

FOREIGN PATENT DOCUMENTS

| | | | |
|---|---|---|---|
| EP | 0255025 | 2/1988 | |
| EP | 0259582 | 3/1988 | |
| EP | 0285424 | 10/1988 | |
| EP | 0311787 | 4/1989 | |
| EP | 0376629 | 7/1990 | |
| EP | 0803267 | 10/1997 | |
| EP | 0819442 | 1/1998 | |
| EP | 0995453 | 4/2000 | |
| EP | 1060730 | 12/2000 | |
| EP | 1484073 | 12/2004 | |
| EP | 1731128 | 12/2006 | |
| FR | 2757405 | 6/1998 | |
| FR | 2780878 | 1/2000 | |
| GB | 1579065 | 11/1980 | |
| JP | 49-12690 | 5/1972 | |
| JP | 62189072 | 8/1987 | |
| JP | 288664 | 7/1990 | |
| JP | 3030963 | 8/1996 | |
| JP | 2000167022 | 6/2000 | |
| JP | 2001505092 | 4/2001 | |
| JP | 2001293085 | 10/2001 | |
| TW | 482670 | 4/2002 | |
| WO | WO 84/04672 | 12/1984 | |
| WO | WO 84/04673 | 12/1984 | |
| WO | WO 90/03536 | 4/1990 | |
| WO | WO 98/19724 | 5/1998 | |
| WO | WO 99/27886 | 6/1999 | |
| WO | WO 99/62578 | 12/1999 | |
| WO | WO 00/05292 | 2/2000 | |
| WO | WO 00/35517 | 6/2000 | |
| WO | WO0035517 A1 * | 6/2000 | A61M 5/00 |
| WO | WO 01/80928 | 11/2001 | |
| WO | WO 02/02048 | 1/2002 | |
| WO | WO 02/11794 | 2/2002 | |
| WO | WO 02/064077 | 8/2002 | |
| WO | WO 02/076540 | 10/2002 | |
| WO | WO 2005/074860 | 8/2005 | |
| WO | WO 2006/082350 | 8/2006 | |
| WO | WO 2006/083333 | 8/2006 | |
| WO | WO 2006/138184 | 12/2006 | |
| WO | WO 2008/115102 | 9/2008 | |

OTHER PUBLICATIONS

Japan Application No. 2003-583539; Official Action dated May 1, 2009 (3 pages).

Japan Application No. 2003-577789, Official Action dated Feb. 24, 2009 (4 pages).

International Search Report, PCT/EP2008/067535 dated Oct. 13, 2009 (3 pages).

International Search Report, PCT/EP2008/067522 dated Aug. 12, 2009. (2 pages).

United States Patent Office, Final Office Action, U.S. Appl. No. 11/762,550, mailed Mar. 17, 2010 (11 pages).

United States Patent Office, Non-Final Office Action, U.S. Appl. No. 11/762,550, mailed Jun. 12, 2009, (11 pages).

* cited by examiner

ARRANGEMENT FOR USE WITH A MEDICAL DEVICE

TECHNICAL FIELD

The invention relates to an arrangement for use with a medical device.

The invention can be implemented in various medical equipments and be used for a number of purposes, but hereinafter the particular, but not in no way limiting for the invention, fields of application constituting an arrangement used together with a device for aseptic preparation of drugs will be described.

BACKGROUND OF THE INVENTION

In the field of drug preparation for injection or infusion generally two basic problems have to be considered. Firstly, certain demands are made on aseptic conditions so as to avoid contamination of the drug, and, secondly, the drug has to be handled in such a way that drug leakage to the environment is prevented or minimized. By a sterile or aseptic handling of the drug, the risk for transferring bacteria or any other undesired substance to the patient is reduced. By preventing drug leakage to the environment, the exposure of medical and pharmacological staff to hazardous drugs is decreased.

In order to achieve aseptic conditions special safety boxes, cabinets or isolators are being used where the air is filtered through HEPA filters to prevent contamination during preparation of drugs. Ventilated cabinets are also used to reduce uncontrolled leakage to the environment and prevent occupational exposure to possibly hazardous drugs. Such facilities, however, require a lot of space and are associated with relatively high costs. Furthermore, the offered protection can be insufficient and working environment problems due to accidental exposure to drugs, for example cytotoxins, have been reported.

Another solution of the problems mentioned above is to create a so called “closed” or “non-vented” system for handling the drugs during preparation. Such systems exist and enable the preparation to be accomplished without the use of special clean rooms or fume cupboards. In such a closed system the drugs are handled isolated from the environment during every single step so as to avoid contamination of the drug and undesired drug leakage to the environment.

A known problem associated with the preparation of drug solutions is the fact that medical bottles or vials normally are made of a non-compressible material, such as glass or plastic. To enable the vial to be drained off, air has to flow into the vial so as to avoid negative pressure in the drug vial which negative pressure otherwise counteracts or prevents further transportation of liquid from the vial to another receptacle such as syringe.

Different systems for providing sterilised or cleaned gas are described for example in WO 00/35517 and WO 02/11794. However, these systems have drawbacks due to the number of manipulations to be accomplished and/or the requisite special equipment for providing the gas.

Within the field of medical devices very often any kind of needle for penetration is used. For example, hollow needles are used for penetration of a closing (which can be made of rubber for instance) covering an opening of a drug vial. Such injection needles or cannulae can be used for enabling gas or liquid transportation between a drug vial and another receptacle. The expression “piercing member” or “needle” used hereinafter is meant to comprise also spikes and similar components for penetration of such a closing in order to create a channel for the transportation of gas or liquid.

A medical device comprising such a needle has drawbacks because the person handling the device can due to incautiousness be injured by the needle. Furthermore, the package enclosing the device can be damaged by the needle during transport and storage of the device. To solve this problem such medical devices can be provided with a needle shield covering the tip of the needle, which shield functions as a protection during storage and the initial handling of the device.

SUMMARY OF THE INVENTION

An object of the invention is to provide an arrangement for use with a medical device, which arrangement can reduce the total number of requisite components and/or provide an additional function to a medical device. In particular, the invention aims to provide such an arrangement suitable for use together with a medical device for providing cleaned gas in a rational and safe way during preparation of drugs.

According to the invention the object is achieved by an arrangement according to claim 1.

By the provision of an arrangement which comprises a shield for a tip of a needle member of a medical device, wherein the arrangement comprises a filter, preferably a particulate air filter for filtering gas to be transferred out from or into the medical device via the needle member when the arrangement is interconnected with the medical device, and the filter is integrated with or constitutes at least a portion of the needle member tip shield, two important functions are provided in one single component. The needle member tip is protected or shielded and gas can be cleaned by means of the filter. Thus, the invention is based on the insight that by providing a needle member tip shield with a filter two functions can be achieved in one and the same component.

According to a preferred embodiment of the invention the needle member tip shield is mainly or entirely constituted by the filter. By manufacturing the needle shield from a filter material a single component having two functions can be obtained in a very rational way.

Further advantages and advantageous features of the arrangement according to the invention are disclosed in the following description and remaining dependent claims.

The invention also relates to a medical device provided with a needle member and an arrangement according to the invention.

BRIEF DESCRIPTION OF THE DRAWINGS

With reference to the appended drawings, below follows a more detailed description of preferred embodiments of the invention cited as examples.

In the drawings.

DETAILED DESCRIPTION OF PREFERRED EMBODIMENTS OF THE INVENTION

Figure 1:
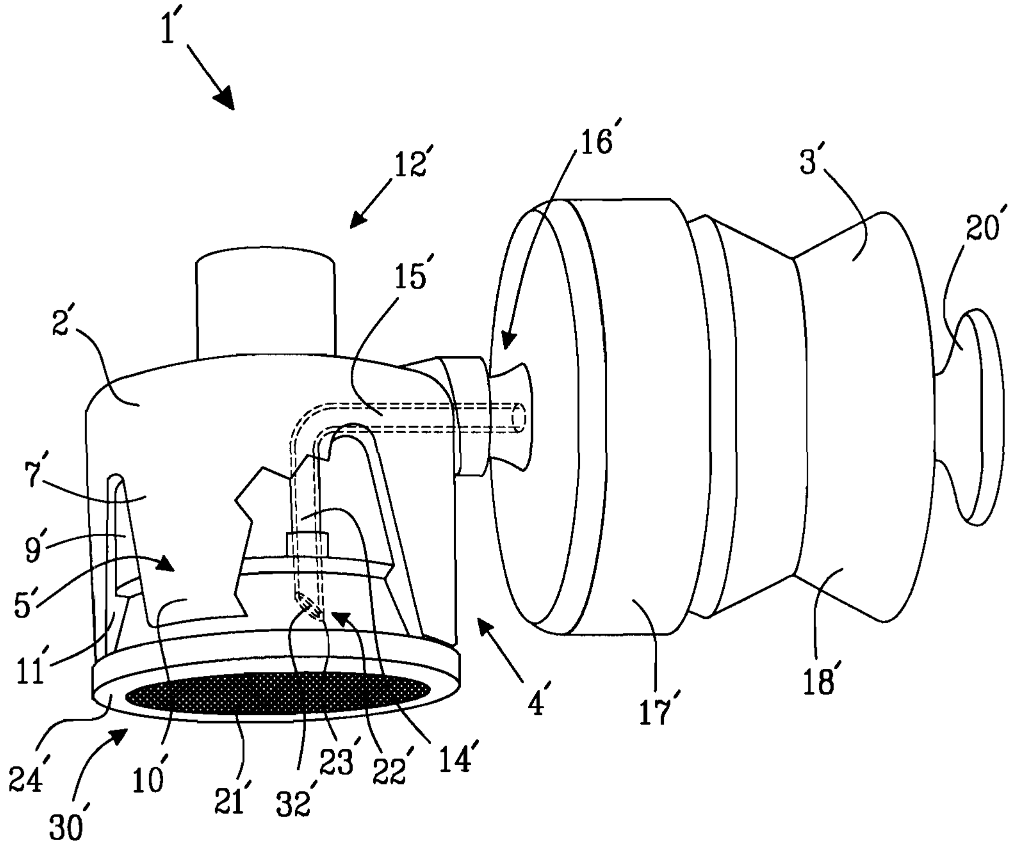
FIG. 1 is a perspective view of a medical device comprising an arrangement according to the invention.
Figure 2:
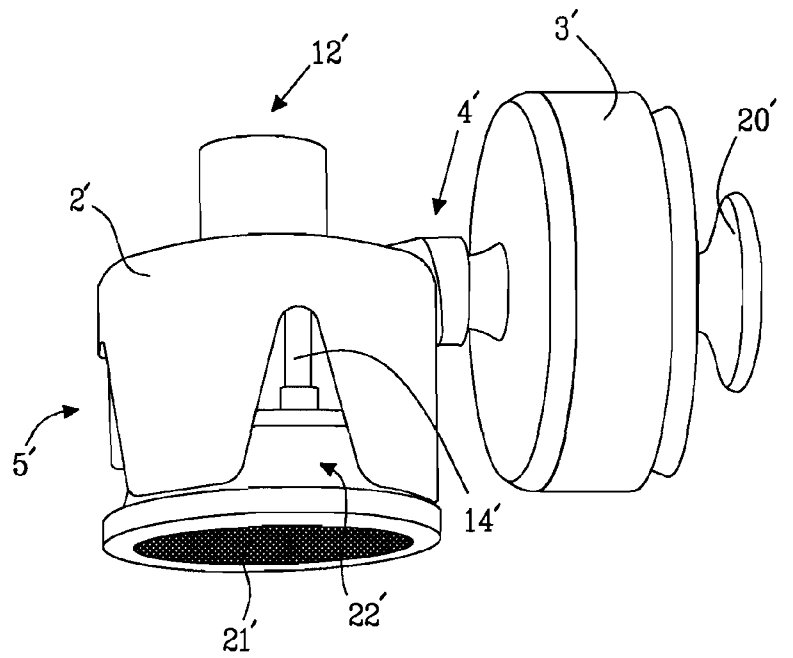
FIG. 2 is a view corresponding to FIG. 1 illustrating the medical device in another condition.
Figure 3:
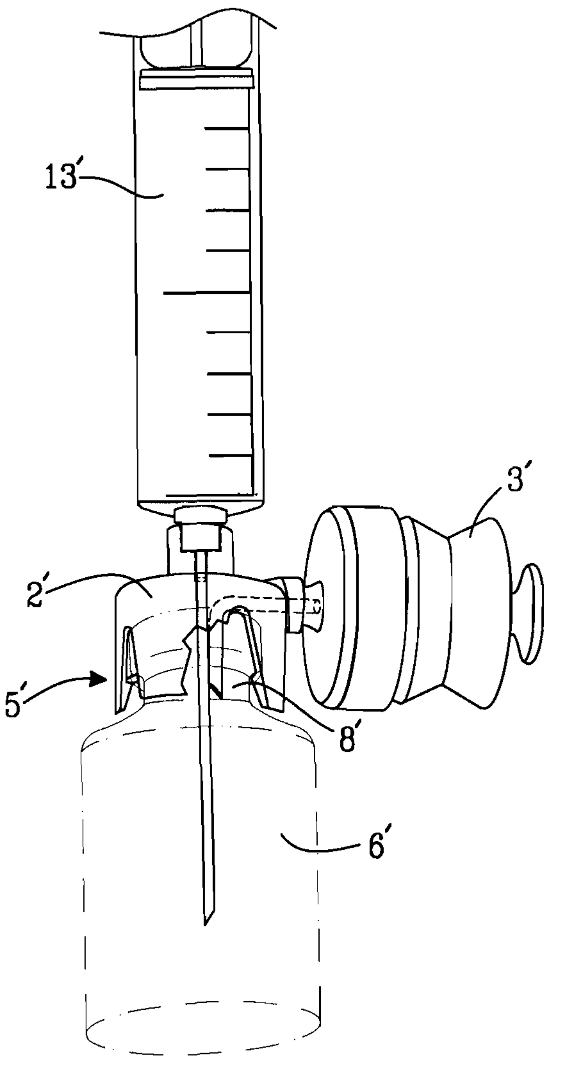
FIG. 3 is a perspective view of the device according to FIG. 1 where the arrangement according to the invention has been removed from the medical device.
Figure 4:
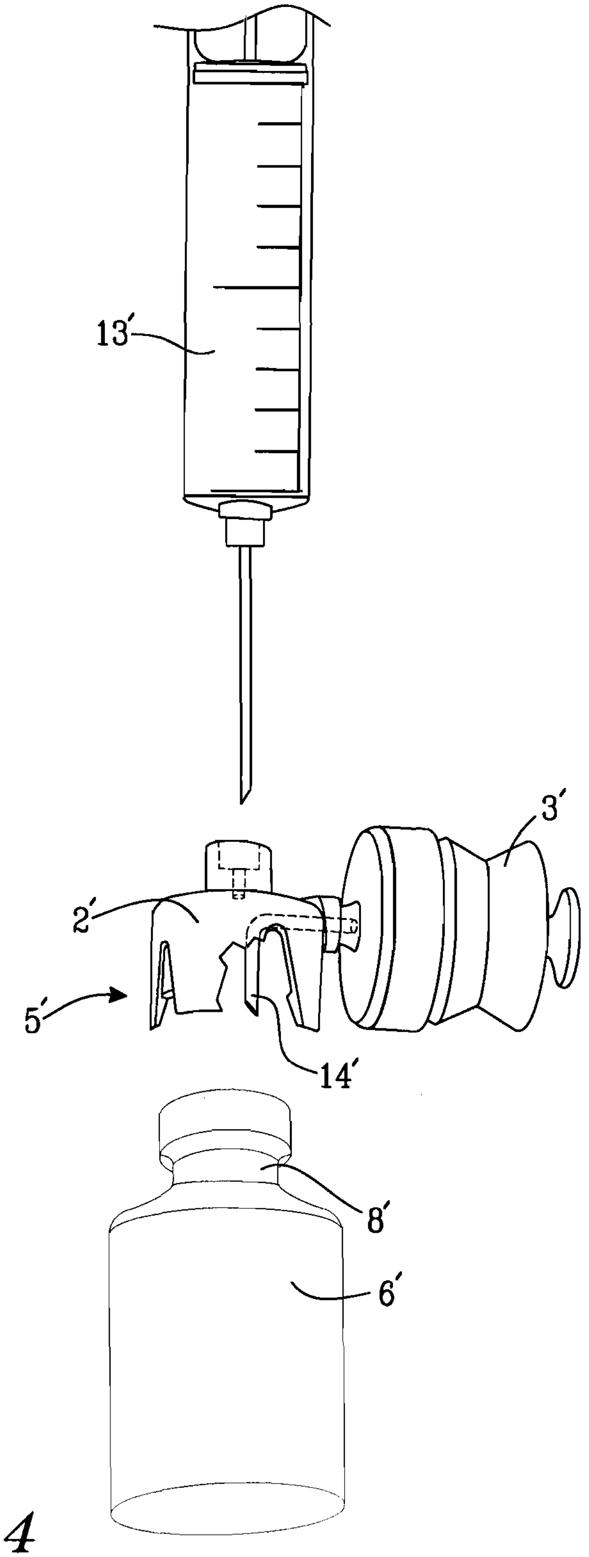
FIG. 4 is an exploded view corresponding to FIG. 3.

In FIGS. 1 and 2 a medical device 1' for providing cleaned gas, for example air, to a receptacle and thereby facilitating conveyance of a substance out of the receptacle is illustrated. Such a substance can be various solutions and liquids constituting drugs, for example cytotoxic drugs or antibiotics, for use in the field of medicine. The device comprises a connector 2' and a container 3' which may form an integrated unit 4'. The connector 2' is provided with a first means 5' for connection to a receptacle 6' or in other words a first connector portion 5'. See also FIG. 3 illustrating the device connected to a medicine bottle or vial 6', and the exploded view in FIG. 4.

The first connection means 5' can be designed for connection to a bottle, such as the neck of a vial. In the embodiment illustrated in FIGS. 1-4, the first connection means 5' is constituted by a ring-shaped portion 7' for enclosing the neck 8' of a vial 6'. The ring-shaped portion 7' has slits 9' so as to form flanges 10' which protrude downwardly. The flanges 10' can be provided with hooks 11' or barbs for gripping around the neck 8' of the vial 6'. The connector 2' is suitably provided with a second means 12' for connection to a transfer member 13' (illustrated in FIGS. 3 and 4), such as an injector device to be interconnected with the connector, for conveyance of a substance out of the receptacle 6', or in other words; the connector 2 is suitably provided with a second connector portion 12'.

In another embodiment the second connection means 12' can comprise a luer lock coupling or bayonet coupling (not shown) to enable an injection device to be connected. Both the injector device and the connector are suitably provided with a membrane so as to create a double membrane coupling between the injector and the current device.

The connector 2' is preferably provided with a piercing member, such as a hollow needle 14' (as illustrated) for penetration of a closing (not illustrated) made of rubber for instance, which closing covers the opening of a receptacle 6, such as vial. In addition to injection needles or cannulae, the expression "needle" is meant to comprise spikes and similar components for penetration of such a closing in order to create a channel for transportation of gas. Herein, a channel between the container 3' and the receptacle 6' to which the connector 2' is connected is created. By a channel or passage 15' of the needle 14', gas contained in the container 3' can be transferred from the container to the receptacle 6', i.e. gas can flow from the container 3' to the receptacle 6'.

The connector 2' and the container 3' may form an integrated unit 4'. This implies that the connector and the container are made in one piece or the connector 2' and the container 3' can be coupled to each other so as to form an integral unit. For such a reason, different types of coupling means 16' known from prior art can be used as long as an airtight, or at least a substantially airtight connection can be obtained between the current components 2', 3'.

The container 3' has to be filled with gas before connection of the connector 2' to a receptacle 6'. The volume of the container 3' is preferably variable. To obtain a container 3' having a variable volume the container can comprise a first portion 17' made by a relatively rigid material which first portion is coupled to the connector 2', and a second portion 18' made by a relatively flexible material attached to the first portion 17'. The second portion 18' can be extensible by manipulation of for example a handle 20' arranged at the end of the container 3'. Hereby the volume of the container 3' can be increased and decreased, respectively. For example, the container 3' can be designed as a bellow which is compressible and extendable by affecting the container manually. The container 3' is preferably provided with said handle 20' for regulating the volume of the container 3'. Although the volume of the container is preferably variable as illustrated, there may be other ways to fill the container and at the same time ensure that the gas passes a filter 21'. For example, the gas container could be constituted by a sealed vacuum-packed flexible bag whose seal can be broken to allow gas to flow into the bag.

Alternatively, the gas container is rigid or semi-rigid and pressurized gas is used to fill the container.

The amount of gas, preferably air, provided by the pre-filled container, should be adapted to the volume of the receptacle which is to be drained off. The volume of the gas when being in the receptacle should preferably correspond to the volume of the receptacle so as to enable the receptacle to be completely drained off. This implies that the volume of the cleaned or sterilized gas in the pre-filled container is preferably approximately equal to or larger than the volume of the receptacle provided that the pressure of the gas is substantially the same in the receptacle as in the container. For most medicine bottles or vials, the volume of the gas should be in the interval 1-100 $cm^3$ at atmospheric pressure.

By the expression "cleaned" gas is meant that the gas has been filtered by a filter, such as a particulate air filter to remove particles and/or viable micro-organisms to such an extent that the gas is classified to be aseptic and accepted by the relevant authority and/or any standards. The degree of purity can be expressed in the largest particles allowed to pass the filter for a given flow rate of gas. In some cases no or very few particles having a size exceeding 5 μm are allowed to occur in the cleaned gas. However, the allowed particle size is determined by the requirements in the current application. Some drug treatments require that substantially all particles having a size exceeding 0.15 μm are removed from the gas by the particulate air filter. As an example, a filter with the mesh size 0.2 μm can be used to remove substantially all particles and micro organisms of that size.

Furthermore, the medical device 1' is provided with an arrangement 30' according to the invention. The arrangement 30' and the medical device 1' are interconnected with each other. In the embodiment illustrated in FIG. 1, the arrangement comprises a shield 22' for covering the tip 23' of a needle member 14' of the medical device 1'. In accordance with the invention a filter 21' is integrated with or constitutes at least a portion of the needle member tip shield 22'. In the illustrated embodiment the filter is arranged to filter the gas to be transferred into the medical device via the needle member 14'. The filter 21' is preferably a particulate air filter, for cleaning gas, such as air to be transferred into the medical device via the needle member 14'. In this example the needle member shield 22' comprises a holder or a frame 24' for accommodating the filter 21', hereinafter called particulate air filter, which frame 24' is connectable to the medical device 1', i.e. to the connector 2'. The main portion of the needle member shield 22' is suitably constituted by the particulate air filter 21' which is arranged for cleaning gas to be transported from the environment into the container 3'. In other words; the particulate air filter 21' is arranged to clean gas which passes the particulate air filter 21' during filling the container 3' with gas (by increasing the volume of the container 3') before connection of the connector 2' to a receptacle 6'. According to the invention the filter is integrated with or constitutes at least a portion of the needle member tip shield. The expressions "integrated with" and "constitutes at least a portion of" are intended to comprise an arrangement where the filter is releasably or permanently connected to the needle member tip shield or is made in one piece with the shield, as well as embodiments where the filter itself constitutes a portion of or the entirely needle member tip shield. Furthermore, in another embodiment of the invention the arrangement could comprise two or more filters.

In a preferred embodiment of the invention the needle member tip shield is adapted to be arranged to at least partially cover or surround the tip of a needle member of a medical device when the arrangement is interconnected with the medical device. This implies that the needle member tip shield covers the tip at least in one direction so as to avoid a user of the arrangement to be injured by the needle due to incautiousness. For example, the shield can be arranged immediately in front of the tip so as to cover the tip in the longitudinal direction of the needle member. The shield can also be designed as a tube, or as a part or parts of a tube, which surrounds the needle tip. Such a shield rather covers the tip in a direction substantially perpendicular to the longitudinal direction of the needle member but extends beyond the tip in the longitudinal direction of the needle and away from the needle member so as to prevent contact with the needle member tip also in the longitudinal direction.

The particulate air filter 21' is preferably adapted to be arranged in front of the tip 23' of the needle member 14' and to at least partially cover or surround the tip of the needle member 14' of the medical device when the arrangement is interconnected with the medical device. As already described, the particulate air filter 21' may be arranged in a frame or holder 24' or similar which in turn fits to the connector 2'. Furthermore, alternatively or in combination, the air particulate filter 21' itself can be designed to be engaged with the connector 2' and/or with the needle member 14', or the particulate air filter 21' can be partly penetrated by the needle member 14' so as to keep the particulate air filter 21' in position. Thus, in one embodiment of the invention the particulate air filter 21' is adapted to be arranged to enclose the tip 23' of the needle member 14' of the medical device 1' when the arrangement 30' is interconnected with the medical device 1'.

Figure 1B:
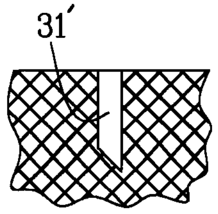
FIG. 1*b* is a cross section view illustrating a portion of a filter having a channel for receiving a needle member.

Instead of being partly penetrated by the needle 14', the particulate air filter 21' can be provided with a channel 31' (illustrated in FIG. 1*b*) for receiving the tip 23' of the needle member 14' therein. In both cases, the particulate air filter 21' preferably encloses the tip 23' of the needle member tightly so as to prevent gas transportation into or out from the needle member 14' without passing the particulate air filter 21'.

In accordance with a preferred embodiment of the invention the particulate air filter 21' is designed and arranged as a protection portion of the needle member shield 22'. This implies that the particulate air filter 21' cleans the gas and at the same time the particulate air filter 21' functions as a protection during handling of the device 1', since the particulate air filter 21' at least partially covers or surround the tip 23' of the needle 14'. Furthermore, the needle member tip shield 22' protects the sterile package enclosing the device during transport and storage of the device.

The particulate air filter 21' is preferably arranged to abut against the needle member tip 23', or rather in immediate contact with the needle portion having an opening 32' for fluid transportation into or out from the needle member 14'. By covering the opening 32' of the needle 14' by means of the particulate air filter 21', it is ensured that the gas which is brought into the container 3' has to pass the particulate air filter 21'. The arrangement and thus the needle member tip shield 22' is preferably adapted to be removably arranged on a medical device 1'. In the illustrated examples the needle member shield 22' is removed before connection of the medical device 1' to a vial 6' as further described hereinafter. The arrangement 30' according to the invention, and, thus the particulate air filter 21' is arranged to be removed from the integrated unit 4' after the container 3' has been filled with cleaned gas. Subsequently to filling the container 3' the particulate air filter 21' is removed and the connector 2' is to be connected to the receptacle 6'. By removing the particulate air filter 21', after the container 3' has been filled with the gas and prior to interconnection of the connector 2' and the receptacle 6' to each other, any contamination particles removed from the gas and collected in the particulate air filter 21' are removed from the integrated unit 4'. Thus, one and the same channel 15' can be used for both filling the container 3' with cleaned gas and transferring the cleaned gas from the container 3' to a receptacle 6'.

Figure 5:
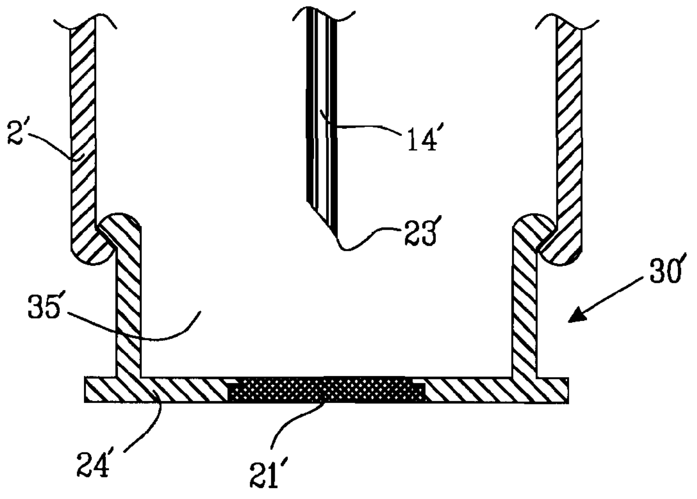
FIG. 5 is a partly cut view illustrating a variant of the arrangement according to the invention.

In FIG. 5 a variant of the arrangement 30' according to the invention is illustrated. The particulate air filter 21' is arranged in a frame 24' to be connected to a medical device and the particulate air filter 21' covers the needle member tip 23'. According to such an embodiment of the invention illustrated in FIG. 5, where the particulate air filter 21' does not enclose the needle member tip 23', but is arranged somewhat spaced apart from the needle member tip 23', the arrangement 30' can preferably be connected to the medical device, for example to the connector 2', so as to obtain a substantially airtight connection between the medical device and the needle member shield 22'. This implies a limited space 35', which space 35' is sealed off relative the environment, being created around the tip 23' of a needle member 14' of the medical device, thereby allowing gas transportation between the space 35' and the environment only via the particulate air filter 21'.

A cover means, for example a lid (not illustrated) can be arranged for covering the particulate air filter, preferably in an airtight manner. The lid may have the function of preventing transportation of liquid, gas or any vapour in the direction from the medical device to the environment or in the opposite direction, i.e. into the medical device from the environment, so as to counteract that any undesired substance in the receptacle escapes to the environment or is introduced into the medical device, respectively.

Such a lid can be used to prevent further communication between the interior of the medical device and the environment via the particulate air filter after the container has been filled. The container can be filled with the cleaned gas and thereafter the lid is mounted to cover the particulate air filter and prevent further gas transportation through the air particle filter. Thereafter, the arrangement can be removed from the medical device and the connector and the receptacle can be interconnected, and the subsequent manipulations can be safely executed.

It is to be understood that the present invention is not limited to the embodiments described above and illustrated in the drawings; rather, the skilled person will recognize that many changes and modifications may be made within the scope of the appended claims.

The invention claimed is:

1. An arrangement for use with a medical device, comprising:

a removably arranged shield for a tip of a needle member of a medical device;

a filter for filtering gas to be transferred out from or into the medical device via the needle member when the arrangement is interconnected with the medical device;

wherein the filter is integrated with or constitutes at least a portion of the shield and is configured to at least partially cover or surround the tip of the needle member of the medical device when the arrangement is interconnected with the medical device;

wherein the medical device comprises a container configured to be filled with gas that is passed through the filter while the medical device is not connected to a receptacle; wherein the container has a variable volume and comprises a first portion made by a rigid material and a second portion made by a flexible material.

2. An arrangement according to claim 1, wherein shield is adapted to be arranged to at least partially cover or surround the tip of the needle member of the medical device when the arrangement is interconnected with the medical device.

3. An arrangement according claim 1 or 2, wherein the filter is adapted to be arranged to cover an opening of the needle member of the medical device when the arrangement is interconnected with the medical device.

4. An arrangement according to claim 1 or 2, wherein the filter is adapted to be arranged to enclose the tip of the needle member of the medical device when the arrangement is interconnected with the medical device.

5. An arrangement according to claim 4, wherein the filter is adapted to be partly penetrated by the tip of the needle member.

6. An arrangement according to claim 4, wherein the filter comprises a channel for receiving the tip of the needle member.

7. An arrangement according to claim 1 or 2, wherein the filter is adapted to be arranged in front of the tip of the needle member of the medical device when the arrangement is interconnected with the medical device.

8. An arrangement according to claim 1 or 2, wherein the shield is mainly or entirely constituted by the filter.

9. An arrangement according to claim 1 or 2, wherein the arrangement is adapted to be removably arranged on a medical device.

10. An arrangement according to claim 1 or 2, wherein the arrangement is adapted to be connected to a medical device so as to obtain an airtight connection between the medical device and the arrangement.

11. An arrangement according to claim 1 or 2, wherein the filter is a particulate air filter.

12. An arrangement according to claim 1 or 2, wherein the arrangement comprises a frame for accommodating the filter, which frame is connectable to a medical device.

13. A medical device provided with a needle member and an arrangement according to any of claims 1-2.

14. A medical device according to claim 13, wherein the arrangement is removably arranged on the medical device.

15. A medical device according to claim 13, wherein the arrangement is arranged on the medical device so as to obtain an airtight connection between the medical device and the arrangement.

16. A medical device according to claim 13, wherein the medical device is a device for providing cleaned gas to a receptacle.

17. A medical device according to claim 13, wherein the medical device is a device to be used in preparation of drugs.

* * * * *